United States Patent [19]

Hessner

[11] 4,231,357
[45] Nov. 4, 1980

[54] BANDAGE FOR ABSORBING BODY FLUIDS

[75] Inventor: Hans Hessner, Djursholm, Sweden

[73] Assignee: Mo Och Domsjo Aktiebolag, Ornskoldsvik, Sweden

[21] Appl. No.: 965,761

[22] Filed: Dec. 4, 1978

[30] Foreign Application Priority Data

Dec. 8, 1977 [SE] Sweden ............................... 7713918

[51] Int. Cl.³ ............................................. A61L 15/00
[52] U.S. Cl. ..................................................... 128/156
[58] Field of Search ................................. 128/155–156, 128/153–154, 283, 285, 296

[56] References Cited

U.S. PATENT DOCUMENTS

| 2,785,677 | 3/1957 | Stumpf | 128/156 |
|---|---|---|---|
| 2,893,388 | 7/1959 | Ganz | 128/156 |
| 2,992,644 | 7/1961 | Plantinga et al. | 128/156 |
| 3,089,488 | 5/1963 | Owens | 128/156 |
| 3,241,553 | 3/1966 | Steiger | 128/285 |
| 3,888,247 | 6/1975 | Stenvall | 128/156 |

Primary Examiner—C. Fred Rosenbaum

[57] ABSTRACT

A body fluid absorbent bandage is provided for open and weeping body wounds, comprising, in combination;
(1) at least two bandage-supporting base layer pieces for juxtaposed attachment to the body about substantially the entire periphery of the wound or injury, and surrounding it, but leaving the wound open and exposed;
(2) an intermediate foraminous sheet for attachment to the base layer as an intermediate layer extending across and bridging the wound; and
(3) an absorbent outer layer for attachment to the intermediate layer in a manner to extend across and cover the intermediate layer at least in the region over the wound within the surrounding base layer, the absorbent outer layer comprising at least in the region over the wound a particulate absorbent material having a water absorptivity of at least 50 mm/10 min according to Klemm, and an envelope of body fluid-pervious sheet material enclosing and retaining the absorbent material in a convex shape at least in the region over the wound; the absorbent outer layer being in a position to absorb body fluids escaping from the wound and passing through the intermediate layer and the enclosing body fluid-pervious sheet material.

12 Claims, 3 Drawing Figures

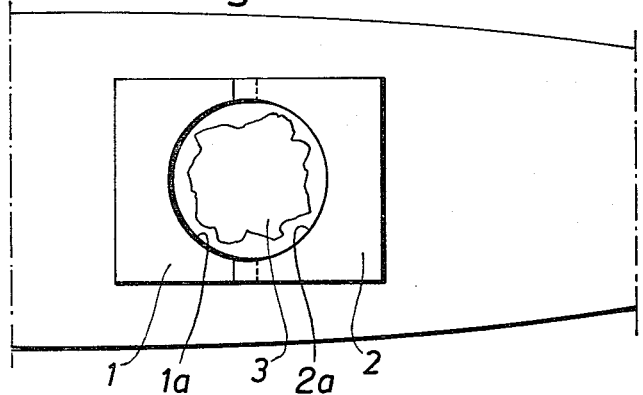
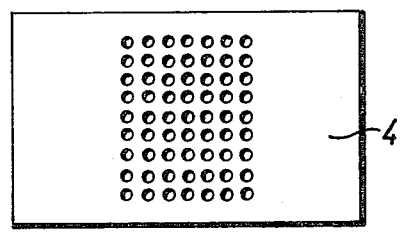
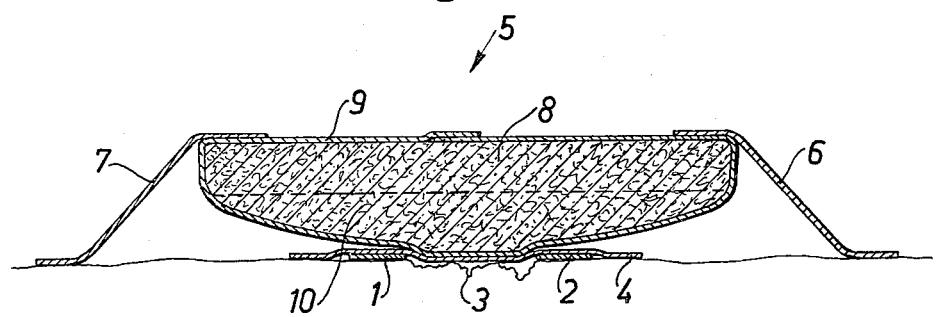

BANDAGE FOR ABSORBING BODY FLUIDS

Open wounds and similar body injuries which secrete or weep copious amounts of body fluid have always posed a formidable bandaging problem. The wound must be protected from bacterial infection, and yet provision has to be made for absorption of the body fluids that escape. While absorbent fabrics are usually used as the bandage material, this requires frequent application of fresh dressings, as each successive dressing becomes saturated.

To decrease the frequency of bandage changes, it has been proposed that a particulate absorbent material be substituted for the conventional fabric bandages. Such a material is dextran, which has a high water absorptivity. The powder is placed directly into the open wound, and as the powder becomes saturated, it is removed and replaced. While the wound is open, the powder can be changed without difficulty, but if a scab or crust is allowed to form after the powder grains or particles are saturated with liquid, removal is difficult without discomfort. Moreover, in all cases the absorbent powder has to be changed frequently, and large amounts of powder are used, which with the necessity of using trained personnel for the handling of the particulate material increases the treatment cost.

The invention provides a body fluid absorbent bandage which utilizes particulate absorbent material but which can be changed frequently without difficulty, even by the patient, and even if a crust has formed over the absorbent material, and without damage to the wound surface. The changing of the bandage is facilitated by enclosing the particulate absorbent material in a protective fluid-permeable envelope, and the adhesion of the absorbent material to the wound is inhibited by suspending the material over the wound surface, spaced from direct contact with the wound by an intermediate foraminous sheet material that spans the wound. The spanning of the wound is made possible by providing a base layer which is attached about substantially the entire periphery surrounding the wound, but without covering over or encroaching upon the wound itself in any way.

The body fluid absorbent bandage in accordance with the invention comprises, in combination, (1) at least two bandage-supporting base layer pieces for juxtaposed attachment to the body about substantially the entire periphery of the wound or injury, and surrounding it, but leaving the wound open and exposed;

(2) an intermediate foraminous sheet for attachment to the base layer as an intermediate layer extending across and bridging the wound; and (3) an absorbent outer layer for attachment to the intermediate layer in a manner to extend across and cover the intermediate layer at least in the region over the wound within the surrounding base layer, the absorbent outer layer comprising at least in the region over the wound a particulate absorbent material having a water absorptivity of at least 50 mm/10 min according to Klemm, and an envelope of body fluid-pervious sheet material enclosing and retaining the absorbent material in a convex shape at least in the region over the wound; the absorbent layer being in a position to absorb body fluids escaping from the wound and passing through the intermediate layer and the enclosing body fluid-pervious sheet material.

In this bandage, the base layer and the intermediate foraminous sheet layer can be left in place until the wound has healed. The only portion that needs to be changed when saturated is the absorbent layer enclosed within the protective liquid-pervious envelope. This not only reduces the cost of changing the bandage, but also facilitates the changing, since the top layer is readily removable without disturbing the intermediate and base layers.

A preferred embodiment of the absorbent bandage of the invention is shown in the drawings, in which:

FIG. a is a top view of the base layer portion of the bandage of the invention, in place on a part of the body surrounding a wound;

FIG. b is a view of an intermediate foraminous sheet of the bandage of the invention; and FIG. c is a longitudinal section through a body fluid absorbent bandage of the invention attached across an open wound in a position to absorb body fluids escaping therefrom.

FIG. a shows an arm A having an open wound 3. Two base layer pieces 1,2 are attached to the arm about the periphery of and surrounding the wound, abutting but not encroaching upon the wound. The base pieces 1,2 have cut out portions 1a,2a which make it possible for them to surround the wound without covering over the wound in any way.

After these pieces have been placed in position, as shown in FIG. a, they are covered over by a foraminous sheet, such as the perforated sheet 4 shown in FIG. b. In place of a perforated sheet a mesh material or netting can be used. This sheet is attached to the base layer either by coating the base layer with adhesive, or coating the sheet with an adhesive, or both. Preferably, the sheet 4 is so open or transparent that the wound can be inspected without removing it. As seen in FIG. c, the sheet 4 bridges the wound between the base layer portions 1,2 but dips into the cavity, and is in actual contact with the wound surface, although it need not be.

The outer or top layer is the absorbent layer 5, composed of particulate absorbent material 8, such as epichlorhydrin-treated cellulose fluff, retained within an envelope of liquid-pervious sheet material, such as a nonwoven fibrous sheet of for example polyamide or polyester fibers. The envelope 9 is so shaped that the absorbent layer has a convex shape in the portion facing the wound, and conforms closely to the contour of the intermediate sheet 4 in this region. If desired, the absorbent material 8 can be composed of a mixture of various absorbent particulate materials, but in any case there is at least 25% of particulate material having a water absorptivity corresponding to a suction height of at least 50 mm/10 min, measured according to Klemm, SCAN P 13:64 (*Papper och Tra* 46 No. 10, pp 603–605 (1964)). The layer in the portion 10 closest to the wound 3 has a water absorptivity of at least 50 mm/10 min, measured according to Klemm.

The absorbent layer can be attached to the body by tapes 6,7 to facilitate removal and replacement with a fresh layer without disturbing the intermediate layer 4 and the base layers 1,2.

The base layer can be formed of two or more pieces of body-adherent nonpervious material so shaped in arcuate configuration or with cut-out portions that when placed in juxtaposition, side-by-side, end-to-end, or overlapping, the entire periphery of the wound is surrounded by the material, while leaving the wound itself open and exposed. The nonpervious material serves as a barrier to the passage of body fluid at the sides of the bandage, when complete, so that the fluids cannot escape from the bandage by this route, and also aids in preventing the entry of bacteria and other harmful contaminants. If the wound is uneven, or has raised portions, it may be advantageous to overlap the base pieces or provide several layers of base pieces to gain a level approximately the same as the wound level.

The base pieces should be placed as close to the edge of the wound as possible, without however encroaching upon the wound area, so as to prevent irritation. The pieces should be thin enough to closely follow the contour of the body.

While the base layer can be applied to the body using a separate application of adhesive, it is of course easier to provide on the base layer pieces a layer of adhesive on one or on both sides. If adhesive is provided on both sides, then the base layer is not only adherent to the skin in itself, but it will also serve to adhere an intermediate foraminous sheet layer to the base layer. To protect such an adhesive layer, a temporary backing sheet that can be provided which is stripped off just before application of the base layer to the body. Such a protective layer is, for example, silicone-treated paper.

The base layer can be formed of any nonpervious sheet material. Adhesive-coated plastic sheets or coated nonpervious fibrous woven and nonwoven material can be used. Preferably, the base layer is of vapor-pervious but not liquid-pervious material, such as (for example) a nonwoven fibrous material coated with adhesive on one or both sides, with the adhesive layers covered by protective paper, such as double layer and single layer adhesive tapes.

After application of the base layer to the body about the wound, the foraminous sheet is then applied, so as to bridge or cover over the wound from the height of the surrounding base layer. The foraminous material can for example be perforated sheet material, or woven and nonwoven or extruded netting of plastic or natural fibers. Animal tissue such as collagen can also be used. The sheet material must be so open or foraminous as not to obstruct the free flow of body fluid from the wound.

Adhesion to the base layer can be provided by an adhesive layer on the base layer, or an adhesive layer on the foraminous sheet material, or both.

To facilitate application of the bandage about a wound, a preformed composite can be used of the foraminous layer and adherent base layer, arranged with a central open or cut-out portion corresponding to the wound. Such composite materials can be provided in standardized shapes and sizes, with various sizes of open or cut out central portions, so as to make it possible to closely approximate the commonly encountered wound sizes.

The foraminous layer can be applied in advance to one of the base layer pieces, and then adhered to the other base layer piece after application to the wound, when the spacing required for the base layer pieces becomes known.

Preferably the foraminous sheet material is transparent or translucent, or so open that one can see through the openings, so that the wound can be inspected through the material without removing it. Suitable materials include polyvinyl chloride, cellophane or regenerated cellulose, polyethylene, polypropylene, polyesters, polyvinylidene chloride, and polyvinyl chloride. The sheet material should not be adherent to the wound, and of course it should be inert to body fluids.

It preferably is applied to such a manner as to be in contact with or close juxtaposition to the wound.

The absorbent layer has a convex shape at the side facing the wound to enable a good contact with the wound surface through the intermediate layer, to facilitate absorption of body fluids, and to fit better within the cavity defined by the base layer surrounding the wound. The convex shape is obtained by the contour of the envelope and the packing of the particulate absorbent material with the envelope.

The liquid-pervious sheet material of which the envelope is formed must have openings or pores large enough to permit the body fluid to pass through without blockage, while small enough to retain the absorbent material therewithin, and it must also be resilient enough to accept the expansion of the absorbent material as it becomes saturated with body fluid. Thus, the material must have a high wet strength, and it must also be inert to the body fluid. Perforated sheet material can be used, as well as nonwoven or woven fibrous sheet material.

It is very important that the absorbent material at least in the region adjacent the wound have a water absorptivity (defined herein as "suction height") of at least 50 mm/10 min, measured according to Klemm, SCAN P 13:64 (*Papper och Tra* 46 No. 10, pp 603–605 (1964)). This is necessary so that the material not only will absorb the body fluid but will also transfer it uniformly throughout the mass of such material. For such transfer, a high water absorptivity alone is inadequate. The transfer capability is measured by the Klemm test in terms of the suction height.

Highly water-absorbent materials which do not meet this suction height limit cannot be used, because they do not transfer the fluid within the mass of absorbent material so as to give a uniform distribution of body fluid throughout the layer. Instead, the body fluid accumulates in the portion of the absorbent layer closest to the wound, which shortens bandage life and also brings about crust formation, which prevents further absorption of the body fluid by the absorbent layer.

The suction height test procedure determines the suction height in mm ten minutes after a vertically suspended strip of paper has been immersed in water in the lower portion. The height is measured in the portion of the paper that is above the water layer. In order to prepare paper for use in such strips, the pulp has to be beaten.

Normally pulped cellulose fibers such as cellulose fluff fibers prepared from sulfite pulp and sulfate pulp do not possess the required suction height according to Klemm. Such material must be further treated, such as for example with a cross linking agent, or in some other way, in order to achieve the desired suction height. As the cross-linking agent, any cross linking agent referred to in U.S. Pat. No. 3,700,549 can be used, including polyhalides, polyepoxides, and polyepoxy halides. A preferred cross-liking agent is epichlorhydrin. In order to obtain an acceptable suction height, the amount of cross linking agent, such as epichlorhydrin cross-linked with the cellulose, must be at least 10% based on the dry weight of the pulp. Such epichlorhydrin cross-linked cellulose pulps can be prepared according to U.S. Pat. No. 3,700,549.

Exemplary different epichlorhydrin cross-linked cellulose pulps which can be used in the absorbent layer of the invention include the following:

| Pulp | Pulp Treatment | Beating (revolutions) | Suction height (mm/10 min) |
|---|---|---|---|
| Bleached Sulfate Birch Pulp | Untreated pulp | 500 | 36 |
| | | 1000 | 25 |
| | | 2000 | 7.5 |
| Bleached Sulfate Birch Pulp | 10% epichlorhydrin | 1000 | 51 |
| | | 2000 | 31 |
| | | 4000 | 12 |
| Bleached Sulfate Birch Pulp | 20% epichlorhydrin | 1000 | 88 |
| | | 2000 | 50 |
| | | 4000 | 20 |
| Bleached Sulfate Pine Pulp | Untreated pulp | 1000 | 40 |
| | | 2000 | 12 |
| | | 4000 | 6 |
| Bleached Sulfate Pine Pulp | 10% epichlorhydrin | 1000 | 69 |
| | | 2000 | 51 |
| | | 4000 | 25 |
| Bleached Sulfate Pine Pulp | 20% epichlorhydrin | 1000 | 76 |
| | | 2000 | 74 |
| | | 4000 | 37 |
| Unbleached Sulfate Pine Pulp | Untreated pulp | 2000 | 28 |
| | | 4000 | 8 |
| | | 7000 | <5 |
| Unbleached Sulfate Pine Pulp | 5% epichlorhydrin | 1000 | 85.5 |
| | | 2000 | 63 |
| | | 4000 | 46 |
| | | 7000 | 17 |
| Unbleached Sulfate Pine Pulp | 10% epichlorhydrin | 1000 | 140 |
| | | 2000 | 118 |
| | | 4000 | 82 |
| | | 7000 | 43 |
| Bleached Sulfite Spruce Pulp | Untreated pulp | 500 | 19 |
| | | 1000 | 10 |
| | | 2000 | 5 |
| Bleached Sulfite Spruce Pulp | 10% epichlorhydrin | 500 | 53 |
| | | 1000 | 33.5 |
| | | 2000 | 16 |
| Bleached Sulfite Spruce Pulp | 20% epichlorhydrin | 1000 | 66 |
| | | 2000 | 28 |
| | | 4000 | 11 |

Table I shows that the suction height values vary with the treatment and the degree of beating. It is apparent from Table I that none of the untreated pulps gives an acceptable suction height, exceeding 50 mm/10 min, regardless of the extent of beating. However, when the pulps are treated with at least 10% epichlorhydrin or more, and are beaten from 500 up to at most about 4000 revolutions in a PFI mill, a suction height exceeding 50 mm/10 min is obtained.

The absorbent layer can be composed of entirely of cross-linked cellulose fluff having the required suction height. However, it may sometimes be satisfactory if only part of the absorbent layer, that portion closest to the wound, is made of such material. If the material will transfer the body fluid away from the wound area, then the necessary distribution is obtained even if the remainder of the layer remote from the wound and to which the body fluid is thus transported is not made of such fluff. In this case, however, the thickness of the layer of cross-linked cellulose fluff should be at least ⅓ the thickness of the entire absorbent layer.

It is also possible to mix with such cross-linked cellulose fluff another highly absorbent particulate material, such as dextran. This makes it possible to achieve the advantages of dextran, but at a lower cost, because of the dilution of this material with cross-linked cellulose fluff, so that only a small proportion of dextran needed, as compared to when all dextran is used. Moreover, the tendency of dextran to form a crust is avoided, because the dextran is interspersed with other material which is noncrust-forming. This makes possible a continued absorption of body fluid even after the material close to the wound has been fully saturated. In these circumstances, the absorption is accommodated by the cross-linked cellulose fluff fibers between the particles of dextran, and these fibers can also have a high capacity to absorb body fluid and transfer it deeper within the absorbent layer.

The alginates can also be used as the absorbent material. Moreover, inorganic absorbents can also be used, provided they have the required suction height, and are nontoxic and nonallergenic.

In addition, the absorbent layer can contain other additives, such as bactericides such as chlorhexidine, fungicides, and other microbicidal materials.

The dimensions of the absorbent body, the intermediate layer and the base layer are of course adapted to the size of the wound that is to be accommodated. In general, however, three sizes of absorbent layer are particularly useful:

(1) rectangular pillow shapes of $5 \times 8 \times$ from about 1 to about 4 cms, (2) rectangular pillow shapes of $8 \times 10 \times$ from about 1 to about 4 cms, (3) square pillow shapes $10 \times 10 \times$ from about 1 to about 4 cms.

When using the body fluid absorbent bandages of the invention, it is not necessary to change the base layer or the intermediate foraminous sheet layer throughout the application of the bandage. The absorbent layer can however be changed as frequently as necessary, without disturbing the other two layers. Moreover, one can simply inspect the wound by removing the absorbent layer and looking through the foraminous sheet layer, if this is transparent as suggested or sufficiently foraminous that one can inspect the wound through the openings. Since the wound does not have to be touched in the exchange of a fresh absorbent layer for the saturated one, the replacement can be done by nonmedically trained staff. Moreover, the patient himself can carry out the necessary inspection and layer change, unlike other bandages utilizing particulate material which place it directly in the wound. Such material is difficult to remove without the aid of trained staff. At the same time, even using trained staff, the treatment of the wound is facilitated, because the bandage is easy to work with, and readily replaced.

The following Example in the opinion of the inventors represents a preferred embodiment of the invention:

EXAMPLE

The bandage illustrated is shown in FIGS. a and c of the drawings.

The two base layer pieces 1 and 2 consist of bandage tape sold under the tradename MICROPORE ® by Minnesota Mining and Manufacturing Co., which tape consists of a nonwoven material provided with a layer of adhesive on the side which is to be secured to the skin. The base layer pieces have the dimension 95×70 mm and are provided with cut-out portions of the shape shown in FIG. a. The adhesive surface is protected with release paper on each of the pieces. The base layer pieces are also on their other (upper) side provided with an adhesive. The pieces 1 and 2 are placed around the wound 3 and adjusted closely to the edges and secured to the skin.

Upon the base layer pieces is placed a plastic netting of a size corresponding to the total surface of the pieces 1 and 2 and of the type sold under the tradename SCRINYL ® by Beghin Say, which consists of parallel polyolefin threads arranged at about 1 mm distance from each other and held together by other polyolefin threads making an angle of 90° with the first threads and placed at a distance of about 8 mm from each other and secured to the first threads in the crossing points by means of heat and pressure. The surface weight of the SCRINYL product is 6–7 g/sq.m.

The absorption layer 5 has the dimension 100×100 mm and a thickness in its central portion of 20 mm and in the edges of 10 mm and corresponds to the shape shown in FIG. c. It consists of a layer 8 of cellulose fluff prepared from bleached sulfite pulp and containing 70% by volume of the layer 5 and a layer 10 of unbleached sulfate pine pulp cross-linked with 10% epichlorhydrin having a water absorptivity according to Klemm of 110 mm/10 min and containing 30% by volume of the layer 5, which is enclosed in an envelope 9 of nonwoven tissue. The absorption layer 5 is provided with two parallel strips of bandage tape 6 and 7 for securing the absorption layer to the skin.

In another suitable form closely related to the one shown in FIGS. a and c, only the base layer piece 1 is provided with adhesive on its upper side, and the plastic netting 4 has the same dimensions as the base piece 1 and is fixed to the base piece 1 in advance.

Having regard to the foregoing disclosure, the following is claimed as the inventive and patentable embodiments thereof:

1. A body fluid absorbent bandage for open and weeping body wounds, comprising, in combination;
   (1) at least two bandage-supporting base layer pieces for juxtaposed attachment to the body about substantially the entire periphery of the wound or injury, and surrounding it, but without covering over the wound or encroaching upon the wound, thus leaving the wound open and exposed;
   (2) an intermediate foraminous sheet for attachment to the base layer as an intermediate layer extending across and bridging the wound; and
   (3) an absorbent outer layer for removable attachment to the intermediate layer in a manner to extend across and cover the intermediate layer at least in the region over the wound within the surrounding base layer, the absorbent outer layer comprising at least in the region over the wound a particulate absorbent material having a water absorptivity of at least 50 mm/10 min according to Klemm, and an envelope of body fluid-pervious sheet material enclosing and retaining the absorbent material in a convex shape at least in the region over the wound, the absorbent layer being in a position to absorb body fluids escaping from the wound and passing through the intermediate layer and the enclosing body fluid-pervious sheet material and being readily removable without disturbing the intermediate and base layers and replaceable by a fresh absorbent layer and envelope.

2. A body fluid absorbent bandage according to claim 1 in which the foraminous sheet is a perforated sheet.

3. A body fluid absorbent bandage according to claim 1 in which the foraminous sheet is a mesh material.

4. A body fluid absorbent bandage according to claim 1 in which the foraminous sheet is sufficiently open or transparent that the wound can be inspected by looking through the foraminous layer upon removal of the absorbent layer.

5. A body fluid absorbent bandage according to claim 1 in which the absorbent material is cross-linked cellulose fluff, retained within an envelope of nonwoven fibrous sheet material.

6. A body fluid absorbent bandage according to claim 1 in which the absorbent layer comprises a mixture of absorbent particulate materials, of which at least 25% is particulate material having a water absorptivity corresponding to a suction height of at least 50 mm/10 min according to Klemm.

7. A body fluid absorbent bandage according to claim 1 in which the absorbent layer comprises a mixture of cross-linked cellulose fluff and particulate dextran.

8. A body fluid absorbent bandage according to claim 1 in which the base layer is formed of at least two pieces of body-adherent nonpervious material shaped in arcuate configuration so that when placed in juxtaposition the entire periphery of the wound is surrounded by the material, while leaving the wound itself open and exposed, and the nonpervious material serves as a barrier to the passage of body fluid at the sides of the bandage.

9. A body fluid absorbent bandage according to claim 8 in which the base layer pieces are provided with a layer of adhesive on at least one side.

10. A body fluid absorbent bandage according to claim 1 in which the foraminous layer and base layer are in the form of a preformed composite arranged with a central open or cut-out portion in the base layer corresponding to the wound.

11. A body fluid absorbent bandage according to claim 1 in which the absorbent layer comprises a first layer in juxtaposition to the wound of particulate absorbent material having a water absorptivity of at least 50 mm/10 min, according to Klemm, and a second layer of particulate absorbent material having a water absorptivity below this limit in fluid-transferring juxtaposition to the first layer.

12. A body fluid absorbent bandage according to claim 1 in which the absorbent layer comprises a microbicidal material.

* * * * *